United States Patent [19]

Fry et al.

[11] Patent Number: 5,712,156
[45] Date of Patent: *Jan. 27, 1998

[54] ENHANCED IMPLANTATION, DEVELOPMENT AND MAINTENANCE OF EMBRYOS USING LEUKAEMIA INHIBITORY FACTOR

[75] Inventors: Richard Charles Fry, Altona North; Ronald Allen Parr, Hoppers Crossing, both of Australia

[73] Assignee: Amrad Corporation Limited, Victoria, Australia

[*] Notice: The term of this patent shall not extend beyond the expiration date of Pat. No. 5,641,676.

[21] Appl. No.: 292,101

[22] Filed: Aug. 17, 1994

Related U.S. Application Data

[63] Continuation of Ser. No. 838,425, filed as PCT/AU91/00307, Jul. 9, 1991, Pat. No. 5,366,888.

[30] Foreign Application Priority Data

Jul. 9, 1990 [AU] Australia .................. PK1064/90

[51] Int. Cl.$^6$ .................. C12N 5/85; C12N 15/86; C12N 15/00
[52] U.S. Cl. .................. 435/325; 435/172.3; 800/2
[58] Field of Search .................. 435/240.1, 240.2, 435/240.21, 172.3, 65.1, 69.7; 800/2; 514/44; 424/93.21

[56] References Cited

U.S. PATENT DOCUMENTS

| | | | |
|---|---|---|---|
| 5,166,065 | 11/1992 | Williams et al. | 435/377 |
| 5,641,676 | 6/1997 | Gough et al. | 435/325 |

FOREIGN PATENT DOCUMENTS

| | | |
|---|---|---|
| WO90/01541 | 2/1990 | WIPO. |
| WO90/08188 | 7/1990 | WIPO. |

OTHER PUBLICATIONS

Bradley et al., 1992. Biotechnology 10: 534–539.
Nichols et al., 1970. Development 110: 1341–1348.
Pease et al. (1990) "Isolation of Embryonic Stem (ES) Cells in Media Supplemented with Recombinant Leukemia Inhibitory Factor (LIF)", *Developmental Biology* 141, 344–352.
Williams et al. (1988) "Myeloid Leukemia Inhibitory Factor Maintains the Developmental Potential of Embryonic Stem Cells", *Nature* 366, 684–687.
Pease et al. (1990) "Formation of Germ–Line Chimeras from Embryonic Stem Cells Maintained with Recombinant Leukemia Inhibitory Factor", *Experimental Cell Research* 190, 209–211.
Smith et al. (1988) "Inhibition of Pluripotential Embryonic Stem Cell Differentiation by Purified Polypeptides", *Nature* 336, 688–690.
Heath et al. (1988) "Regulatory Factors of Embryonic Stem Cells", *J. Cell. Sci. Suppl.* 10, 257–266.
Hilton et al. (1988) "Purification of a Murine Leukemia Inhibitory Factor from Krebs Ascites Cells", *Analytical Biochemistry* 173, 359–367.

*Primary Examiner*—Brian R. Stanton
*Attorney, Agent, or Firm*—Scully, Scott, Murphy & Presser

[57] ABSTRACT

Disclosed is the in vitro development of mammalian embryos to the implantation stage by culturing the embryos in a medium containing leukemia inhibitory factor (LIF). Inclusion of LIF in the medium containing embryos also enhances the ability of the embryos to develop normally.

12 Claims, No Drawings

ENHANCED IMPLANTATION, DEVELOPMENT AND MAINTENANCE OF EMBRYOS USING LEUKAEMIA INHIBITORY FACTOR

This is a continuation of application Ser. No. 838,425, filed on Apr. 16, 1992, now U.S. Pat. No. 5,366,888, issued Nov. 28, 1994 International Application PCT/AU91/00307, filed on Jul. 9, 1991 and which designated the U.S.

The present invention relates to the use of Leukaemia Inhibitory Factor (LIF) in the enhancement of development and maintenance of animal or mammalian embryos and the use of same to enhance impregnation.

LIF is a protein that has previously been cloned, produced and purified in large quantities in recombinant form from both *E. coli* and yeast cells (International Patent Application No. PCT/AU88/0093). LIF has been defined as a factor, the properties of which include:

1. the ability to suppress the proliferation of myeloid leukaemic cells such as M1 cells, with associated differentiation of the leukaemic cells; and
2. the ability to compete with a molecule having the defined sequence of murine LIF or human LIF (defined in International Patent Application No. PCT/AU88/00093) for binding to specific cellular receptors on M1 cells or murine or human macrophages.

A major difficulty associated with present in vitro fertilisation (IVF) and embryo transfer (ET) programs, particularly in humans, is the low success rate "achieved" on implantation of fertilised embryos. Currently, in human IVF programs, the implantation rate may be as low as 10%, leading to the present practice of using up to four fertilised embryos in each treatment which, in turn, leads occasionally to multiple births. Accordingly, there is a need to improve the implantation rate in human IVF programs. Similarly, in IVF and ET treatments in domestic animals such as sheep, cattle, pigs and goats, it is highly desirable for economic reasons to have as high an implantation rate as possible so as to reduce the numbers of fertilised embryos lost and unsuccessful treatment procedures performed. Furthermore, as with human IVF procedures, the practice of transferring more than one embryo to the recipient animal to ensure pregnancy can result in unwanted multiple births.

One major constraint with embryo transfer is the need to hold embryos in culture media for either relatively short periods of time, perhaps only a few hours prior to transfer or for longer periods of some days, after micromanipulation.

In the development of a mammalian embryo, the fertilised egg passes through a number of stages including the morula and the blastocyst stages. In the blastocyst stage, the cells form an outer cell layer known as the trophectoderm (which is the precursor of the placenta) as well as an inner cell mass (from which the whole of the embryo proper is derived). The blastocyst is surrounded by the zone pellucida, which is subsequently lost when the blastocyst "hatches". The cells of the trophectoderm are then able to come into close contact with the wall of the uterus in the implantation stage. Prior to formation of the embryo proper by the inner cell mass by gastrulation, the whole cell mass may be referred to as "pre-embryo".

Embryo mortality has been attributed to incomplete hatching of the blastocyst from the zona pellucida and/or unsuccessful implantation of the embryo to the uterine wall, possibly due to spontaneous differentiation of the embryonic stem cells (ES) during their period in culture prior to transplantation.

In accordance with the present invention, it has been found that when LIF is included in an in vitro embryo culture medium, the hatching process is enhanced leading to an increased number of embryos completing the development stage by undergoing developmental changes associated with implantation. Thus, LIF is an embryo protective agent. As a result, the implantation rates for IVF and ET programs can be, and are, significantly improved by the use of LIF in the in vitro embryo culture medium.

Furthermore, media containing LIF is suitable for use in early manipulative procedures on the oocyte/embryo such as in vitro fertilisation, embryo splitting and nuclear transfer where survival rates of embryos are low. LIF also has important applications in the growth of totipotent stem cell lines for cloning for inclusion into the media used for the transport of cooled or frozen embryos/semen.

Unless otherwise specified, use of "LIF" herein refers to synthetic recombinant or naturally occurring human, murine and/or livestock or ruminant LIF, such as from sheep, pigs, cows, goats, donkeys and horses and from other animals such as dogs, cats or birds (eg. chickens) and to derivatives or parts thereof. Such derivatives or parts thereof include any one or more contiguous series amino acids contained within any one of the above LIF molecules and includes single or multiple amino acid substitutions, deletions and/or additions to or in the natural or synthetic LIF molecule. Conditions for preparing recombinant LIF are disclosed in International Patent Application Nos. PCT/AU88/00093 and PCT/AU90/00001 although variations and/or modifications to these conditions may vary depending on the host cell used. Any such variations and/or modifications are within the scope of the subject invention. The host cells may be eukaryotic (eg. yeast, mammalian, insect, plant etc.) or prokaryotic (eg. *Escherichia coil, Bacillus sp, Pseudomonas sp* etc.) cells.

Accordingly, one aspect of the present invention contemplates a method for enhancing the impregnation rate in an animal with one or more embryos said method comprising maintaining and/or developing the embryos in a medium containing an effective mount of leukaemia inhibitory factor (LIF) for sufficient time and under appropriate conditions and then implanting the embryos into the animal.

By "impregnation" means the rate of successful implantations and subsequent development of a fertilised embryo in vivo.

Another aspect of the present invention contemplates a method for maintaining embryos or pre-embryos in in vitro culture while retaining viability for use in embryo transfer, IVF and/or genetic manipulation which method comprises culturing said embryos in a medium containing an effective amount of LIF for sufficient time and under appropriate conditions.

This method of maintaining the viability of embryos in culture has potential for allowing genetic manipulation of the whole embryo. Such successful genetic manipulation is restricted at the present time due to the limited amount of time available to perform experiments on viable embryos.

The method also may be advantageous in maintaining viability of embryos under transport conditions and may also be beneficial in the storage of embryos when compared to techniques currently employed.

Another aspect of the present invention relates to a method for enhancing the in vitro development of a mammalian embryo to the implantation stage, which method comprises the step of culturing the embryo in vitro in a culture medium containing an effective amount of mammalian LIF.

As is demonstrated below the inclusion of LIF in the culture medium prior to the formation of the blastocyst, or both prior to and following blastocyst formation, also increases the number of pre-embryos completing the developmental stage by undergoing development changes associated with implantation. The addition of LIF also reduces the number of pre-embryos degenerating while in culture. As a result, the implantation rate for IVF and ET programs can be significantly improved by use of LIF in the in vitro culture medium.

"Animal embryos" is used in its broadest sense encompassing embryos from mammals such as humans, ruminant and other livestock animals and other animals such as birds and fish. It will be appreciated that while the subject invention is exemplified herein by the development ovine embryos in vitro the present invention extends to the use of LIF in the development of embryos of other animal or mammalian species including humans, ruminants and animals such as cattle, horses, donkeys, goats and the like.

The present invention, also extends to a method for in vitro fertilisation and subsequent implantation of a mammalian embryo which is characterised in that the embryo is cultured in vitro in a culture medium containing an effective amount of mammalian LIF prior to transfer into animal or mammalian host, where "host" is defined as a suitably receptive female animal or mammal.

A further aspect of the present invention relates to a non-human animal and in particular a chimaeric non-human animal or transgenic progeny of said animal generated by known techniques using ES cells which have been maintained in vitro in LIF-containing culture medium. In accordance with this aspect of the present invention, ES cells are derived from animal embryos passaged in a culture medium containing LIF wherein said ES cells have additional genetic material inserted therein. The transgenic animals contemplated include non-human mammals such as livestock and ruminant animals and domestic animals.

In accordance with the present invention, "homologous" or "heterologous" systems may be employed meaning that the animal from which LIF is derived is the same animal (homologous) or a different animal (heterologous) from which the embryos are isolated. The LIF may be naturally occurring but is preferably recombinant or synthetic LIF. The LIF may be of any origin such as human, murine or livestock animal (including ruminant animal) LIF provided that the LIF has the desired effect. It may be, for example, that a LIF from one animal may not be as active as a LIF from another animal. It is within the skill of the addressee to readily screen for suitable LIFs from appropriate animals. Where recombinant LIF is used, it may be produced in eukaryotic or prokaryotic cells.

The present invention is also directed to composition comprising an effective amount of LIF in combination with an animal (eg. mammalian) embryo maintaining medium. The present invention also provides a composition having embryotrophic and/or embryo protective properties comprising LIF in combination with one or more of ovine trophoblast protein, Interleukin 1 and/or 2, macrophage colony stimulating factors, platelet activating factor, a factor in the murine fibroblast 3T3 line and/or plasminogen. The above composition may also be in combination with an embryo maintaining medium.

An embryo maintaining medium as contemplated herein includes but is not necessarily limited to SOF and/or M2.

The mount of LIF used in accordance with the present invention is that required to maintain and/or develop embryos and/or enhance impregnation and is in the range of 100 units/ml to 10,000 units/ml, preferably 500 units/ml to 5,000 units/ml and most preferably from 1,000 units/ml to 5,000 units/ml. A unit of LIF activity is defined in PCT/AU88/00093.

The present non-limiting examples further illustrate the present invention:

EXAMPLE 1

Materials and Methods

Embryo Collection

Forty mature Merino ewes were treated for 14 days with a CIDR containing 0.3 g progesterone (Riverina Artificial Breeders, NSW) and were superovulated by the injection (i.m.) of 5 mg of the pituitary follicle-stimulating hormone FSH-P (Intervet Australia Pty, Ltd, Sydney, NSW) and 200 iu of PMSG (i.m.) (Pregnecol; Heriot Agvet Pry, Ltd, Melbourne, Vic) 48 h before CIDR withdrawal, followed by decreasing doses of FSH-P (4, 3, 3, 2, and 1 mg) every 12 h afterwards. Ovulation was ensured by a 50 µg injection (i.m.) of Gonadotrophin-Releasing hormone (GnRH; Auspep Pry, Ltd, Melbourne, Vic) 24 h after CIDR withdrawal, which coincided with the time that most ewes were detected in oestrus by vasectomised rams fitted with marking crayons. Ewes were inseminated via a laparoscope with approximately $100 \times 10^6$ fresh motile sperm into each uterine horn 8–12 h after oestrus. The semen was collected from 4 fertile rams, diluted 1:1 in phosphate buffered saline (Flow Laboratories, North Ryde, NSW) and kept at ambient temperature prior to insemination. Six days after oestrus the ewes were anaesthetised with an injection (i.v.) of the barbiturate sodium thiopentone (Intraval: May & Baker, Footscray, Vic) and maintained under general anaesthesia by a mixture of halothane (May & Baker) and oxygen. The uterus was exteriorised by a mid-ventral laparotomy and each horn was cannulated with a Foley catheter (Promedica, Moorabin, Vic) at approx. 1 cm below the bifurcation. A 20 g needle attached to a 20 ml syringe filled with flushing media was passed into the lumen of the uterus near the uterotubal junction. Each horn of the uterus was flushed and the media plus embryos were collected into glass vessels via a Foley catheter. Embryos were pooled in M2 holding media containing 4 mg/ml Miles BSA (Pentex Crystalline; Miles Diagnostics, Kanakee, Ill., USA) and graded according to health and stage of development before allocation to treatment groups.

Culture of Embryos

Embryos (166 assessed as healthy and 17 as poor quality) were randomly allocated to one of three treatment groups. Embryos in treatment 1 (80 healthy and 5 poor quality embryos at the morula or early blastocyst stage) were cultured in lots of 10 for 1–2 h in 5 ml of M2 holding media prior to being transferred either as pairs (Group 1; n=38) or singularly (Group 2; n=47) into recipient ewes at Day 6 of the oestrous cycle. Group 3 embryos (44 healthy and 6 poor quality embryos at the morula or early blastocyst stage), were cultured individually in SOF media for 48 h prior to transfer. Three separate 100 μl droplets of SOF culture media were placed in a 35×10 mm plastic Petri-dish and covered with 2.5 ml paraffin oil (Labchem, Ajax Chemicals, Auburn, NSW). One embryo was then placed in each droplet and the Petri-dishes were placed in a waterjacketed incubator and were maintained at 39° C. in an atmosphere containing 20% $O_2$, 5% $CO_2$ and 75% $N_2$. Group 4 embryos (44 healthy and 6 poor quality morula or early blastocysts) were cultured for 48 h in SOF culture media as for Group 3 except that human recombinant LIF was added to the media at a rate of 1000 units/ml).

The number of healthy or poor quality (degenerating) embryos, those achieving morula, blastocyst or hatching blastocyst stage of development was recorded at the time of embryo collection, every 12 h afterwards and immediately prior to transfer to recipient ewes at Day 8 after oestrus.

Culture Media

The flushing media used was Dulbecco's phosphate buffered saline containing 10% (v/v) foetal calf serum, Penicillin G. potassium salt (0.060 g/l) and Streptomycin sulphate (0.050 g/l).

M2 culture media (Quinn et al. 1982) was a modified Krebs-Ringer solution with some of the bicarbonate substituted with HEPES buffer. The components were HEPES buffer (4.969 g/l), NaCl (5.533 g/l), KCl (0.356 g/l), $CaCl_2.2H_2O$ (0.252 g/l), $KH_2PO_4$ (0.162 g/l), $MgSO_4.7H_2O$ (0.293 g/l), $NaHCO_3$ (0.349 g/l), Penicillin G. potassium salt (0.060 g/l), Streptomycin sulphate (0.050 g/l) made up to 1 litre with Millipore $H_2O$.

SOF culture media (Tervit et al., 1972) consisted of NaCl (6.95 g/l), KCl (0.534 g/l), $KH_2PO_4$ (0.162 g/l), $CaCl_2.2H_2O$ (0.252 g/l), $MgCl_2.6H_2O$ (0.10 g/l), $NaHCO_3$, (2.106 g/l), Na lactate (0.616 g/l), Na pyruvate (0.0363 g/l), Glucose (0.270 g/l), BSA (32.0 g/l), Penicillin G. potassium salt (0.060 g/l), Streptomycin sulphate (0.050 g/l) made up to 1 litre with Millipore $H_2O$.

All media was sterilised by filtration through a 0.2 μm filter (Millipore Pty, Ltd, Richmond, Vic).

Embryo Transfer

Two hundred 3 year old maiden Merino ewes had their oestrous cycles synchronised with a 14 day CIDR treatment. An injection of 400 UI PMSG was given at the time of CIDR withdrawal. Vasectomised rams, fitted with harnesses and crayons were placed with the ewes to detect oestrus. Ewes observed in oestrus were randomly allocated to one of 4 recipient groups. Recipient ewes were treated with local anaesthetic (lignocaine, Lyppard Chemicals, Brighton, Vic) and using laparoscopy, the number of corpora lutea on each ovary was recorded. The uterus was located and the tip of the uterine horn, ipsilateral to an ovulating ovary was exteriorised through a 2 cm mid-ventral incision. The uterus was punctured approximately 4 cm from the tip and the embryo, bathed in Ms holding media was deposited via a Tomcat catheter (Size 3.5 FR, Lyppard Chemicals, Brighton, Vic) attached to a 1 ml syringe. The uterine horn was returned into the abdominal cavity and the incision sutured.

All recipient ewes were grazed with harnessed vasectomised rams for 21 days to provide an estimate of embryonic loss prior to or at implantation (Edey, 1967). Ewes were scanned using ultrasonics on Days 70 of pregnancy to determine the number of healthy foetuses.

Analysis

Differences between groups were determined by Chi-square analysis.

EXAMPLE 2

Effect of LIF on in vitro Development of Ovine Embryos to the Post-Hatching Stage Embryo Culture The addition of 1,000 units/ml of human recombinant LIF to SOF culture media significantly improved the development (more blastocysts hatching and less degenerating) of healthy morula and blastocyst embryos cultured for 48 h in vitro (Table 1).

Both treatment groups had 6 embryos initially classified as poor at the time of embryo recovery. Over the treatment period their health did not improve so they were discarded and not transferred to recipient ewes.

Implantation Rates

When the cultured embryos were individually transferred to recipient ewes the 21-day non return rate (an indicator of implantation rate) of ewes receiving an embryo that had been cultured in SOF+LIF (Group 4) was significantly higher than that of ewes receiving an embryo culture in SOF alone (Group 3: Table 2). Furthermore, the implantation rate of the Group 4 ewes was similar to recipient ewes that had received a single embryo within 2 h of collection (group 2), but the non-return rates of both groups were lower than that of recipient ewes that had two embryos transferred soon after collection (Group 1).

Actual pregnancy rates, as determined by real time ultrasonic scanning on Day 70 of pregnancy are shown in Table 3.

The results given above demonstrate that the addition of human recombinant LIF to culture media increases up to 4-fold the number of ovine blastocysts that "hatch" from the zona pellucida and decrease the number of embryos degenerating during their 48 h culture in SOF at an atmosphere of 20% $O_2$, 5% $CO_2$ and 75% $N_2$. In fact 64% of the embryos cultured in SOF+LIF had hatched by Day 8 after oestrus which is similar to that found in vivo (Rowson and Moor, 1966, Bindon, 1971). LIF may have a role in maintaining the health of embryos under adverse conditions. Furthermore, during this period of culture the pregnancy rates of the recipient ewes after the transfer of embryos cultured in media containing LIF for 48 h was at least equal to that of ewes receiving an embryo immediately after collection.

This stabilising role of LIF on embryos agrees with the recent reports of the localisation of LIF receptors on the Day 4 murine embryo and of murine LIF being expressed strongly in the endometrial glands of the Day 4 pregnant and pseudopregnant mouse. This suggests that LIF is produced as a passive response to pregnancy rather than to the presence of the embryo. LIF therefore appears to be produced at the time that the embryo is entering the uterus from the oviduct. The results herein suggest that some of the embryonic mortality reported at around this time could be averted by an adequate supply of LIF to the embryo. Currently, in most embryo transfer programs in both humans and livestock animals, more that one embryo is transferred to each recipient to ensure a viable pregnancy. Our study indicates that pregnancy rates are almost 40% higher when 2 embryos are transferred to each ewe even though there is still about a 50% loss of embryos (52% of these ewes had twins, 37% had singles and 11% were not pregnant). Hence, there is a possibility that LIF could prevent some of this embryonic loss and effectively make the transfer of a single embryo to each recipient practical.

TABLE 1

Number and percentage of healthy embryos hatching or degenerating during 48 h culture in media SOF (n = 42) or SOF + 1000 units/ml LIF (n = 44).

| Time in Culture | Hatched Embryos SOF | | SOF + LIF | | Degenerating Embryos SOF | | SOF + LIF | |
|---|---|---|---|---|---|---|---|---|
| 0 h | 0 | 0% | 0 | 0% | 0 | 0% | 0 | 0% |
| 12 h | 0 | 0% | 3 | 7% | 2 | 5% | 0 | 0% |
| 24 h | 1 | 2% | 10* | 23% | 2 | 5% | 1 | 2% |
| 36 h | 6 | 14% | 19* | 43% | 5 | 11% | 1 | 2% |
| 40–46 h | 7 | 16% | 28* | 64% | 13* | 27% | 4 | 9% |

*Denotes significant differences between SOF & SOF + LIF treatment groups P < 0.05.

TABLE 2

Ewes returning to service within 21 days after oestrus.

| | Group 1<br>1 Embryo<br>3 h in M2 | Group 2<br>2 Embryos<br>3 h in M2 | Group 3<br>1 Embryo<br>48 h in SOF | Group 4<br>1 Embryo<br>48 h<br>in SOF + LIF |
|---|---|---|---|---|
| Returned to service | 0 | 13 | 26 | 15 |
| Not returned to service | 19 | 28 | 18 | 27 |
| Total | 19 | 41 | 44 | 42 |
| % Not Returned | 100$^a$ | 68$^b$ | 41$^c$ | 64$^b$ |

Different superscripts denote significant differences (P < 0.05).

TABLE 3

Number of recipient ewes pregnant at Day 70 after oestrus.

| | Group 1<br>1 Embryo<br>3 h in M2 | Group 2<br>2 Embryos<br>3 h in M2 | Group 3<br>1 Embryo<br>48 h in SOF | Group 4<br>1 Embryo<br>48 h SOF + LIF |
|---|---|---|---|---|
| Non-pregnant | 2 | 20 | 37 | 21 |
| Pregnant | 17 | 22 | 7 | 21 |
| Total | 19 | 42 | 44 | 42 |
| % Pregnant | 89$^a$ | 52$^b$ | 16$^c$ | 50$^b$ |

Different superscripts denote significant differences (P < 0.05).

EXAMPLE 3

The use of LIF in Embryo Culture and Transfer

Ovine embryos were collected from merino ewes 6 days alter oestrus as described above. This time, however, they were cultured individually for 10 days in either SOF, SOF+ murine LIF or SOF+human LIF and development assessed daily. The intention was to see if and how far the embryos developed post hatching in media containing LIF such as whether they reach the expanded blastocyst or trophoblast stages of development which occurs at around Days 10–12 in vivo Secondly, the effect of murine LIF on the development of cultured sheep embryos was also investigated.

Embryos were collected from merino ewes in exactly the same manner as in Example 1. The only difference being that the ewes were superovulated by either the FSH products Ovagen or RFSH-50 supplied by Horizon Reproduction. The treatments were:

Group 1 (n=19); Embryos cultured individually in SOF alone.

Group 2 (n=18); Embryos cultured individually in SOF+ murine LIF. mLIF added at 3500 units/ml by mouse stem cell bioassay which equates to approx. 8000 units/ml using the M1 cell bioassay.

Group 3 (n=20); Embryos cultured individually in SOF+ human LIF (hLIF). hLIF added at 5000 units/ml by MI cell bioassay.

The culture conditions were identical to the above examples except that embryo development was assessed daily rather than twice daily. The atmospheric condition were as described above, i.e. 20% $O_2$, 5% $CO_2$, and 75% $N_2$. The results are shown in Table 4.

TABLE 4

| Treatment | Days in Culture | | | | | | | | | | |
|---|---|---|---|---|---|---|---|---|---|---|---|
| | 0 | 1 | 2 | 3 | 4 | 5 | 6 | 7 | 8 | 9 | 10 |
| SOF | 10B | 19B | 13B | 11B | 1HB | 1HB | 19D | | | | |
| | 9M | | 6D | 8D | 9B | 5B | | | | | |
| | | | | | 9D | 13D | | | | | |
| SOF + mLIF | 9B | 4M | 18B | 15B | 14B | 11B | 20D | | | | |
| | 9M | 14B | | 3D | 4D | 7D | | | | | |
| SOF + | 10B | 4HB | 4FB | 12FB | 14FB | 14FB | 14FB | 14FB | 12FB | 11FB | 20D |

TABLE 4-continued

| | \multicolumn{11}{c}{Days in Culture} |
|---|---|---|---|---|---|---|---|---|---|---|---|
| Treatment | 0 | 1 | 2 | 3 | 4 | 5 | 6 | 7 | 8 | 9 | 10 |
| hLIF | 10M | 16B | 9HB 5B 2D | 7HB 2B 2D | 4HB 1B 3D | 2HB 1B 3D | 1B 5D | 1B 5D | 8D 8D | 9D 9D | |

Legend:
M = morula
B = blastocyst
HB = hatching blastocyst
FB = blastocysts free from the zona pellucida
D = degenerating embryos After 3 days in culture significantly more embryos had developed to hatching or had completely hatched from the zona pellucida when placed in SOF+hLIF (Group 3) than those embryos in SOF (Group 1) or SOF+mLIF (Group 2) (P<0.01, Chi-square). Furthermore, significantly less had degenerated after 6 days in culture (P<0.01, Chi-square). There was no significant effect of mLIF on the development or survival of the embryo. None of the blastocysts that had hatched from the zone pellucida had commenced to elongate prior to degeneration.

EXAMPLE 4

This example details a repeat of Example 2 but placing the embryos in fresh media every second day in an attempt to induce further development of the hatched blastocyst.

The treatments were as follows and the results are shown in Table 5.
Treatments:
Control—SOF
Group 1—SOF+mouse LIF (5000 units/ml by M1 bioassay)
Group 2—SOF+human LIF (5000 units/ml by M1 bioassay)

TABLE 5

| Treat-ment | \multicolumn{9}{c}{Days in Culture} |
|---|---|---|---|---|---|---|---|---|---|
| | 0 | 1 | 2 | 3 | 4 | 5 | 6 | 7 | 8 |
| SOF n = 8 | 2B 6M | 2B 6M | 2B 5M 1D | 8D | | | | | |
| SOF + LIF n = 8 | 3B 5M | 8B | 1HB 5D 3D | 8D | | | | | |
| SOF + hLIF N = 8 | 3B 5M | 1HB 5B 2M | 2FB 3HB 1B 1M 1D | 5FB 1HB 2D | 6FB 2D | 6FB 2D | 6FB 2D | 8D | |

This experiment again demonstrates that hLIF improved the health of morula and blastocysts held in culture. While the hatched blastocysts grew from about 1 mm to 2mm they did not commence to elongate.

EXAMPLE 5

The aim of this example was to investigate if the addition of LIF to SOF culture media improves the health of very early stage embryos.

In this experiment, embryos were taken from donor ewes at various times after oestrus and cultured for specific periods of time in SOF or SOF+hLIF (1000 units/ml) before their development was assessed by counting their number of cells. All embryos (excepting those of group 5) were cultured in atmospheric conditions of low $O_2$ tension (7%) to allow the earliest stage embryos to pass through the 8/16 cell block. Embryo health was assessed by spreading the cells on a slide and ciunying cell numbers.
Treatments:
Group 1. 2–4 cell embryos collected 2 days after oestrus and cultured for 6 days in either SOF (n=10) or SOF+hLIF (n=14).
Group 2. 2–4 cell embryos collected 2 days after oestrus and cultured for 2.5 days in either SOF (n=15) or SOF+hLIF (n=18).
Group 3. 8/16 cell embryos collected 4 days after oestrus and cultured for 2 days in either SOF (n=11) or SOF+hLIF (n=9).
Group 4. Morula/blastocysts collected 6 days after oestrus and cultured for 2 days in either SOF (n=19) or SOF+ hLIF (n=20).
All these embryos were cultured in the specific atmosphere of 7% $O_2$, 5% $CO_2$, 88% $N_2$.
Group 5. Morula/blastocysts collected 6 days after oestrus and cultured for 2 days in either SOF (n=19) or SOF+ hLIF (n=18).
These embryos were cultured in an atmosphere of 20% $O_2$, 5% $CO_2$, 75% $N_2$. In other words this group is a repeat of the embryos cultured in Examples 2, 3 and 4.

The results are shown in Table 6.

TABLE 6

| Treatment | Mean cell number (±sem) SOF | SOF + hLIF |
|---|---|---|
| Group 1 | 41.2 ± 3.94 | 69.1* ± 8.42 |
| Group 2 | 7.4 ± 0.52 | 8.5 ± 0.60 |
| Group 3 | 17.7 ± 1.94 | 24.9 ± 5.20 |
| Group 4 | 75.7 ± 10.40 | 82.7 ± 11.49 |
| Group 5 | 56.2 ± 5.90 | 62.6* ± 8.42 |

*Denotes significant differences between groups within rows (P < 0.05) Students t-test.

In summary, this experiment shows that the addition of hLIF to the culture media improves the health when they are held under sub-optimal conditions i.e. less than ideal atmospheric conditions (Group 5) or for long periods of time under improved atmospheric conditions (Group 1).

EXAMPLE 6

The aim of this example was to determine if the addition of hLIF to the transfer media improves the subsequence implantation rates of recipient ewes.

In this experiment embryos were collected from superovulated Merino ewes 6 days after oestrus. They were placed in either SOF or SOF+hLIF (5000 units/ml) and individually intransferred to recipient ewes either within 1 h of collection or after being held for between (5–8 h in the media at 39° C. The embryos were transferred in the culture media. The pregnancy rates were confirmed by ultrasonic scanning 65 days after oestrus.

The results are shown in Table 7.

TABLE 7

| Group | Media | Time in culture | Pregnant | Not Pregnant |
|---|---|---|---|---|
| 1 | SOF | <1 h | 21 (58%ᵃ) | 15 |
| 2 | SOF + LIF | <1 h | 21 (51%ᵃ) | 20 |
| 3 | SOF | 6–8 h | 8 (21%ᵇ) | 30 |
| 4 | SOF + LIF | 6–8 h | 21 (53%ᵃ) | 19 |

Different superscripts denote significant differences ($P < 0.01$; Chi-square)

This experiment demonstrates that hLIF has little effect upon implantation rates if the embryos are transferred immediately after collection. However, if the embryos are left in culture for between 6–8 h prior to transfer, which quite often is the situation in the field, the addition of hLIF to the media maintains the viability embryos which would otherwise have degenerated.

EXAMPLE 7

In a commercial ET program, 248 recipient Merino or Crossbred ewes each received 2 embryos that had been held in either M2 or M2 +hLIF (5000 units/ml). The culture time varied from about 1 to about 6–8 hours. The donor ewes were Merinos.

The results are shown in Table 8.

TABLE 8

|  |  | N | 2 Embryos | 1 Embryo | Not Pregnant |
|---|---|---|---|---|---|
| M2 | Merinos | 148 | 44 | 40 | 64 |
|  | Xbred | 20 | 10 | 4 | 6 |
|  | Total | 168 | 54 (32%) | 44 (26%) | 70 (42%) |
| M2 + LIF | Merinos | 56 | 24 | 12 | 20 |
|  | Xbred | 44 | 24 | 7 | 13 |
|  | Total | 100 | 48 (48%) | 19 (19%) | 33 (33%) |

Embryo Mortality:
M2=55%
M2+LIF=43%

The addition of LIF to the M2 culture media significantly increased the implantation rates ($P<0.05$: Chi-square). This indicates that LIF has potential as an embryo protective agent when added to media used for ET programs.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

REFERENCES

Bindon, B. M. (1971) Systematic study of preimplantation stages of pregnancy in the sheep. *Aust. J. biol. Sci.* 24: 131–147.

Edey, (1967) *J. Reprod. Fertil.* 13: 437–443.

Quinn, P., Barros, C. and Whittington, D. G. (1982) Preservation of hamster oocytes to assay the fertilising capacity of human spermatozoa *J. Reprod. Fert.* 66: 161–168.

Rowson, L. E. A. and Moor, R. M. (1966) Development of the sheep conceptus during the first fourteen days. *J. Anat.* 100: 777–785.

Tervit, H. R., Whittington, D. G, and Rowson, L. E. A. (1972) Successful culture in vitro of sheep and cattle ova. *J. Reprod. Fert.* 30: 493–496.

We claim:

1. A method for maintaining one or more mammalian, avian, or fish embryos in an in vitro culture that permits normal morphological development of said embryos in vitro, the improvement comprising culturing said one or more mammalian, avian, or fish embryos in a medium containing an effective amount of leukemia inhibitory factor (LIF) for a sufficient time and under appropriate conditions to permit normal morphological development of said one or more embryos.

2. The method according to claim 1 wherein the mammal is a human.

3. The method according to claim 1 wherein the mammal is a ruminant.

4. The method according to claim 1 wherein the LIF is of mammalian origin.

5. The method according to claim 4 wherein the LIF is of human, murine, or ruminant origin.

6. The method according to claim 4 or 5 wherein the LIF is recombinant or synthetic LIF.

7. The method according to claim 6 wherein the LIF is produced in a eukaryotic cell in vitro.

8. The method according to claim 6 wherein the LIF is produced in a prokaryotic cell in vitro.

9. The method according to any one of claims 1 to 5 wherein the effective amount of LIF is from about 100 units/ml to about 10,000 units/ml.

10. The method according to claim 9 wherein the effective mount of LIF is from about 500 units/ml to about 5,000 units/ml.

11. The method according to claim 10 wherein the effective mount of LIF is from about 1,000 units/ml to about 5,000 units/ml.

12. The method according to claim 1, wherein the medium is SOF and/or M2 medium.

* * * * *